United States Patent [19]
Bradley

[11] Patent Number: 5,730,372
[45] Date of Patent: Mar. 24, 1998

[54] APPARATUS AND METHOD FOR PRODUCING BONE GRAFT MATERIAL

[76] Inventor: Christopher Mark Bradley, 21 Phillipps Street, Somerton Park, South Australia, Australia

[21] Appl. No.: 638,791

[22] Filed: Apr. 29, 1996

[30] Foreign Application Priority Data

Apr. 28, 1995 [AU] Australia ................... PN 2638

[51] Int. Cl.$^6$ ............... B02C 19/05; B02C 19/12
[52] U.S. Cl. .............. 241/29; 241/152.2; 241/169.1; 241/169.2
[58] Field of Search ............ 241/29, 30, 152.2, 241/169.2, 169.1, 283, DIG. 27, 199.9, 199.11, 199.12

[56] References Cited

U.S. PATENT DOCUMENTS

| | | | |
|---|---|---|---|
| 4,209,135 | 6/1980 | Starks .................. | 241/169.1 X |
| 4,341,356 | 7/1982 | Hiott et al. ............ | 241/169.2 |
| 4,397,425 | 8/1983 | Moore et al. ........... | 241/169.2 X |

FOREIGN PATENT DOCUMENTS

| | | | |
|---|---|---|---|
| 2057245 | 6/1993 | Canada .................. | 241/169.2 |
| 261263 | 10/1988 | German Dem. Rep. ....... | 241/169.2 |

*Primary Examiner*—Mark Rosenbaum
*Attorney, Agent, or Firm*—Brown, Martin, Haller & McClain, LLP

[57] ABSTRACT

The invention is directed to a method and apparatus for producing bone graft material for use in conjunction with bone grafting procedures wherein fragments of bone material are placed within a hollow receptacle (12) which has a periphery wall defining a milling chamber and a removable base plate (11) which is releasably secured by fasteners (13) to the open bottom end of the receptacle (12). A crushing tool (18) slidably engages within the chamber and is caused to impact against the bone fragments so as to consolidate same into a solid physical mass, whereafter the consolidated crushed bone material is machined or ground using a spherical reamer (22) attached to a power drill (23). Preferably the bone material is crushed by means of a hammer (20) which is manually impacted against the top end of the crushing tool (18).

13 Claims, 2 Drawing Sheets

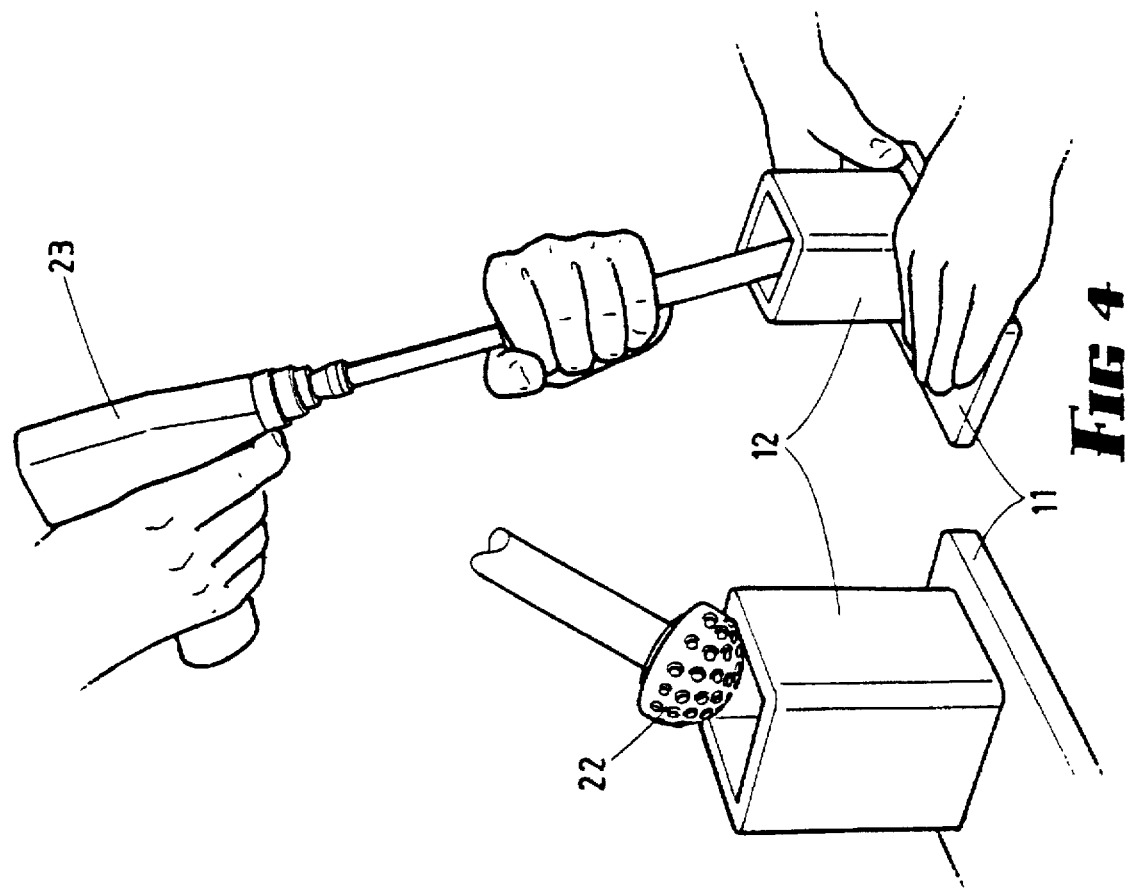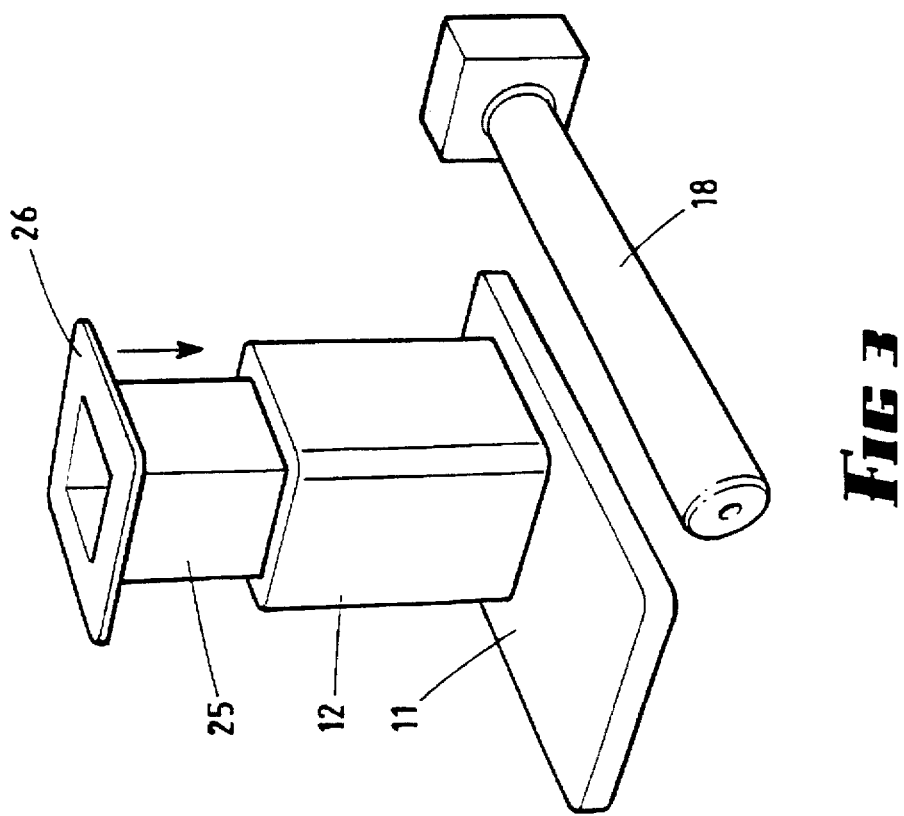

APPARATUS AND METHOD FOR PRODUCING BONE GRAFT MATERIAL

The present invention relates to apparatus and a method for producing bone graft material.

Modern techniques of reconstructive orthopaedic surgery especially those associated with bone loss have allowed, with the judicious combination of modular implants and large bone grafts, procedures which have hitherto not been feasible. With a legacy of some twenty years plus of cemented implants, the symptoms of failure of which may not become apparent until significant bone stock destruction has occurred, the modern day orthopaedic surgeon engaged in reconstructive joint surgery and similar areas is faced with a requirement to efficiently produce bone graft material for use in combination with the foregoing implants.

Evidence indicates that reconstruction by a combination of morsellated bone and structural assemblies eg implants etc offers greater long term success than if some type of structural bone block allograft is used in the same circumstance. This is especially true about the pelvis following failure of previously implanted hip replacement devices where a very large cavitary defect is frequently combined with loss of the anterior and posterior columns of the pelvis. Such columnar support can be readily obtained utilising internal fixation devices, the cavitary defect remaining and requiring significant volumes of bone graft (of the order of cubic inches of said graft).

Concurrent with these major bone grafting requirements there is always a requirement in joint fusion surgery, and for that matter in cases of joint re-alignment surgery where bone defects are to be re-established, for small quantities of bone graft material to be made readily available to the operator, frequently requiring a second incision about the pelvis, in spite of the presence of (hitherto otherwise useless) bone fragments taken at the time of such correction (eg wedges of bone from osteotomies etc).

Current bone grafting procedures may utilise allograft (ie stored bone) or autograft (ie bone obtained at the time of the surgery) or most commonly a combination of both.

In order to prepare the bone substrate for the most appropriate utilisation (viz rapid incorporation of small morsellated fragments exceeds any incorporation of larger fragments, and offers more suitable biologic reconstruction accordingly), the modern day orthopaedic surgeon is faced with simple mechanical difficulties in obtaining same. The current bone grafting machinery mostly consists of a "food-processor style" or rotating cylindric shaving system in which the bone is fed into a series of cutting faces with such limitation of pressure and compaction as such devices dictate, the load/power available to the operator often being in the form of a windlass with a hand winding motion or alternatively with a small electric or air powered motor unit.

The quality of the material obtained thereby and the speed at which it is obtained, are both low.

A typical unit is a relatively large structure which requires assembly, has rotating bearings etc which all then require disassembling/cleaning and frequently will have a high heat capacity disallowing immediate or recurrent use during the course of procedures.

Particularly, utilisation of small bone fragments either from the allograft bank or from sections of bone removed at the time of corrective surgery is all but impossible with these devices.

SUMMARY OF THE INVENTION

The present invention represents a significant departure from current practice in that bone either allograft or autograft as the case may be is compressed in a chamber and then processed within it with as much force as can be obtained by an operator utilising standard operating equipment eg spherical hip reamers. Apart from the speed at which the graft material is obtained using this method, the advantage of being able to utilise small fragments compressed into a useful solid mass and then machined within the unit is of great significance in that bone graft donor sites associated with spinal fusion surgery can thereby be entirely eliminated. Sufficient bone can be created with the device to fuse as many levels as are operated on simply by resecting posterior elements and machining them within the device, thereby eliminating long term donor site morbidity, the commonest cause of dissatisfaction with spinal fusion procedures at long term follow-up.

According to one aspect therefore of the present invention, apparatus for producing bone graft material comprises an open-ended receptacle, a base plate releasably attachable to the open bottom end of the receptacle, the receptacle and base plate, when attached thereto, defining a chamber having a closed bottom end and an open upper end for receiving fragments of bone material, and a separate crushing tool positionable in the chamber through its open upper end and arranged, in use, to impact against fragments of bone material in the chamber to thereby condense the bone fragments into a solid physical mass.

In a second aspect of the present invention, a method of producing bone graft material, comprises: placing fragments of bone material within a hollow chamber having a closed bottom and an open top, locating an impacting tool within the chamber, manually crushing the bone material within the chamber by impacting the tool against the bone fragments so as to consolidate the bone fragments into a solid physical mass, and grinding the consolidated crushed bone material within the chamber by means of a power tool to produce the bone graft material.

Generally, the bone material will be crushed using an impaction tool in conjunction with a hammer, and then ground (morsellated) using a reamer.

Preferably, the crushing tool comprises an elongate handle and an enlarged impact head at the bottom end of the handle, the impact head being sized so as to form a close fit with the walls of the chamber.

Preferably, the bore of the chamber and the impact head of the bone crushing tool are rectangularly shaped.

Preferably, spikes are provided on the base plate for holding the bone material during the compaction and/or grinding process. The height of the spikes is chosen to ensure non-interference with the coulter of the reamer during the grinding process.

The apparatus of the present invention can be used to produce morsellated autograft and allograft for use in conjunction with bone grafting procedures of all kinds. The apparatus has particular advantages when used in relation to reconstructive surgery, such as major hip reconstructive surgery and knee reconstructive surgery, where volume defects are to be compensated for by a combination of modular implants together with allograft/autograft bone stock replacement. With judicious use of a cavity reduction system, small fragments of bone chipped away at the time of primary surgery, or otherwise during the course of exposure of various parts of the skeleton later to be bone grafted, may be prepared for grafting using the apparatus and method of the present invention. The apparatus and method is used to condense bone fragments into a solid physical mass, which is then machined, for example by using a standard spherical reamer, such as that as supplied by Osteonics Corp (USA), in order to produce quality "shavings" of bone graft.

BRIEF DESCRIPTION OF THE DRAWINGS

The apparatus of this invention is easy to assemble and disassemble, has no moving parts or bearings that need replacement and is essentially maintenance free. The apparatus will now be described in more detail with respect to a particular embodiment, as illustrated in the accompanying drawings, in which:

FIG. 3 illustrates the use of a sleeve insert, to reduce the effective size of the chamber; and FIG. 4 shows the apparatus being used for grinding bone material, using a reamer.

DESCRIPTION OF THE PREFERRED EMBODIMENT

Figure 1:
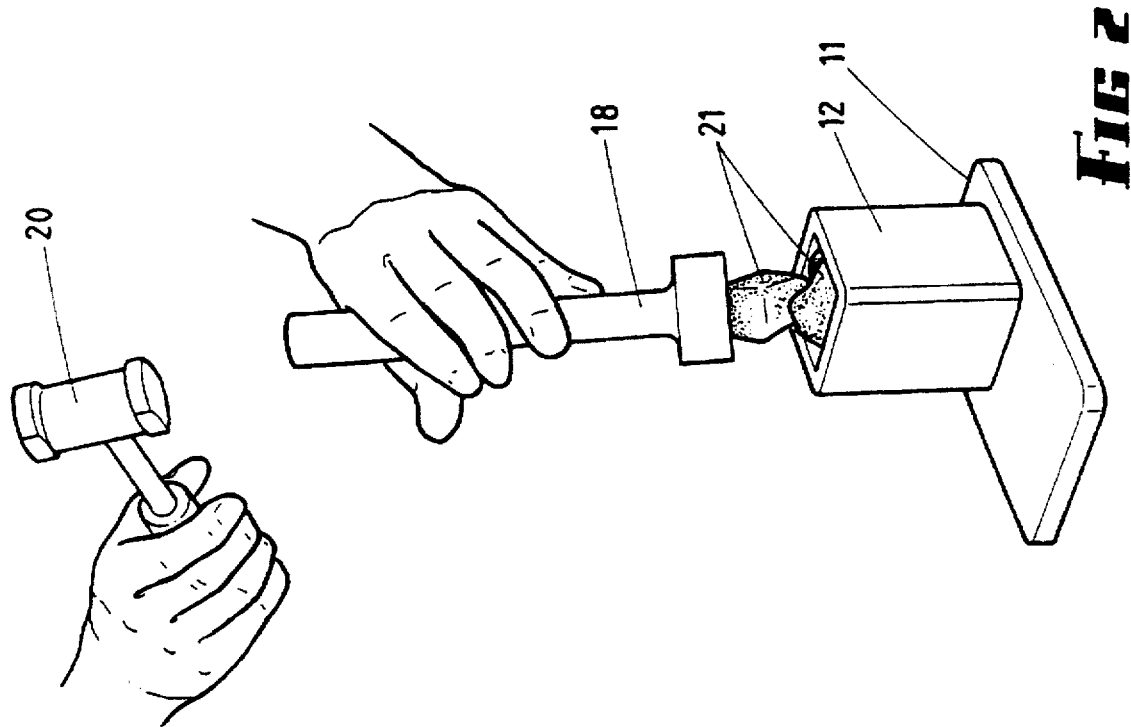
FIG. 1 is an exploded view of the apparatus according to a preferred embodiment of the invention.
Figure 2:
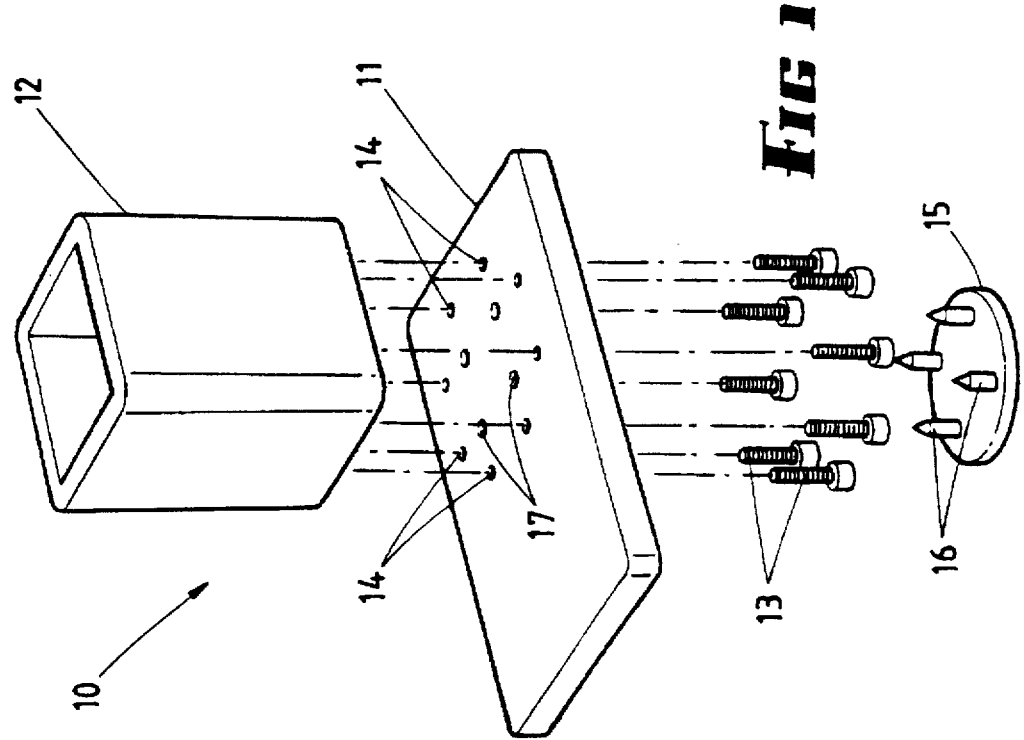
FIG. 2 shows the apparatus in assembled form, being used for the compaction of bone material.

Referring to FIGS. 1 and 2 of the drawings, the apparatus 10 essentially comprises a stainless steel base plate 11 to which an open-ended rectangular shaped receptacle 12, also of stainless steel, is securely fastened, e.g. by means of clamping bolts 13 which pass through holes 14 formed in the base plate 11 and into threaded blind bores (not shown) formed in the bottom end face of the receptacle 12. Preferably, the receptacle 12 is positioned to one end of the base plate 11 to allow the base plate to be held, either manually as shown in FIG. 4 or by mechanical fastening means, against a support surface in order to secure the apparatus against movement, during compaction and/or grinding of the bone material.

The base plate 11 of the apparatus is readily removable from the receptacle 12, by simply unscrewing the bolts 13 eg by means of an Allen key. This allows the individual parts of the apparatus to be completely cleaned after use, prior to re-sterilisation etc.

In order to securely hold the bone material within the chamber of the receptacle 12 during the compaction or grinding process, there is provided a spiked disc 15 having upstanding spikes 16. In this embodiment, the underside of base plate 11 has been machined to form a locating recess for receiving the disc 15 so that it lies flush with the underside of the base plate 11. The spikes 16 locate through corresponding apertures 17 in the base plate 11, and project into the interior of the receptacle 12. The spikes 16 assist to retain bone material, in particular spherical bone elements such as femoral heads etc, within chamber 12 and also to prevent the spherical bone elements from rotating with the cutting member of the spherical reamer used to grind the material after crushing. Alternatively, instead of utilising a separate removable spiked disc 15, fixed spikes may be incorporated on the upper surface of base plate 11.

As shown in FIG. 2, a heavy crushing or compaction tool 18 in conjunction with a hammer 20, is used to crush the fragments 21 of bone material placed in the chamber of the receptacle 12 into a solid physical mass.

After compaction of the bone material, as shown in FIG. 2, the consolidated bone material is machined or ground within the receptacle 12 using a known spherical reamer 22 attached to a power drill 23. The machining or grinding stage is shown in FIG. 4.

If only a small amount of bone material is available, or a small fragment of bone is to be machined, a sleeve insert 25 (as shown in FIG. 3) is used to reduce the effective internal dimensions of the milling chamber 12. The insert 25 has a top peripheral flange 26 which, when the insert is slidingly fitted in the chamber, abuts against the top end face of the receptacle 12.

The apparatus of the present invention is extremely easy and convenient to use. The apparatus is assembled, and bone is taken from an allograft bank in the case of an allograft reconstruction, or from blocks of bone or from femoral heads taken at the time of hip surgery etc in the case of an autograft reconstruction. After impaction (see FIG. 2), the standard spherical hip reamer 22 is used to reduce the compacted bone to morsellated allograft/autograft respectively (see FIG. 4). The process can be achieved in seconds, and the entire apparatus is readily assembled so that almost instantaneous use of the device is possible.

Preferably, the device is constructed from materials, such as stainless steel, having low heat capacity and cold water/saline submersibility. This allows the apparatus to be cleaned and re-sterilised between use, or if necessary flash sterilised and made available to the operating surgeon immediately on demand.

Most prior attempts at allograft femoral head grafting have produced small fragments rather than shavings, because insufficient pressure can be placed on the bone graft material to achieve a length of cut by the spherical reamer sufficient to produce actual shavings.

The structure of the present apparatus is sufficiently strong to withstand normal levels of abuse, and in particular the significant impact loads occasioned by the impaction stage shown in FIG. 2.

By making use of the sleeve insert 25 shown in FIG. 3, even small fragments of bone which would otherwise be useless to the bone grafting operation can be re-deployed after the crushing step in the reduced size chamber, and then machined into worthwhile graft material.

It should be noted that, while the present invention has been described in terms of a preferred embodiment in order to facilitate better understanding of the invention, various modifications can be made without departing from the principles of the invention. Therefore, the invention should be understood to include all such modifications within its scope.

I claim:

1. Apparatus for producing bone graft material, comprising:

an open-ended receptacle;

a base plate releasably securable to the open bottom end of the receptacle, the receptacle and base plate when attached to said receptacle defining a chamber having a closed bottom end and an open upper end for receiving fragments of bone material;

a separate crushing tool insertable in said chamber through its open upper end and arranged, in use, to impact against fragments of bone material in the chamber to thereby condense the bone fragments into a solid physical mass; and a plurality of mutually spaced apart upstanding spikes on said base plate and which project a short distance upwardly into said chamber, said spikes being arranged to immobilise bone material within the chamber.

2. Apparatus according to claim 1, wherein said crushing tool comprises an elongate handle and an enlarged impact head at the bottom end of said handle, said impact head being shaped and sized so as to form a close fit with the walls of said chamber.

3. Apparatus according to claim 1, wherein said receptacle and said base plate are releasably secured together by means of threaded bolts which locate through holes formed in the base plate and into threaded blind bores formed in the bottom end face of said receptacle.

4. Apparatus according to claim 1, wherein said spikes are secured to a separate carrier plate and project upwardly through spike locating holes formed in the base plate so that their upper ends project into the interior of said chamber.

5. Apparatus according to claim 4, wherein said carrier plate locates in a recess formed in the underside of said base plate so that it lies flush therewith.

6. Apparatus according to claim 1 wherein said receptacle is secured to said base plate non-centrally thereof.

7. Apparatus according to claim 1 wherein said receptacle and said base plate are formed of stainless steel.

8. Apparatus for producing bone graft material, comprising:

an open-ended receptacle;

a base plate releasably securable to the open bottom end of the receptacle, the receptacle and base plate when attached to said receptacle defining a chamber having a closed bottom end and an open upper end for receiving fragments of bone material;

a separate crushing tool insertable in said chamber through its open upper end and arranged, in use, to impact against fragments of bone material in the chamber to thereby condense the bone fragments into a solid physical mass; and a tubular sleeve insert removably engageable within said chamber for reducing the cross-sectional area of the chamber, said insert having a peripheral flange at its upper end arranged to abut against the upper end face of the receptacle, said insert having a shape corresponding to that of the chamber.

9. Apparatus according to claim 8, wherein said chamber is rectangularly shaped.

10. A method of producing bone graft material comprising:

placing fragments of bone material within a hollow chamber of a receptacle having a closed bottom and an open top, locating a crushing tool within the chamber, impacting the tool against the bone fragments so as to crush and consolidate same into a solid physical mass, and grinding the consolidated crushed bone material within the chamber by means of a power hand tool to produce the bone graft material.

11. A method according to claim 10, wherein the impact crushing tool comprises an elongate handle and an enlarged impact head at the bottom end thereof, the step of locating a crushing tool within the chamber comprises slidably locating the impact head within said chamber.

12. A method according to claim 11, wherein the step of impacting the crushing tool against the bone fragments comprises impacting a manually operated impact hammer against the upper end of the tool.

13. A method according to claim 10, wherein the step of grinding the consolidated crushed bone material within the chamber is effected by means of a reamer attached to a drill bit of a hand drill.

* * * * *